United States Patent [19]

Reinhardt et al.

[11] Patent Number: 4,919,147

[45] Date of Patent: Apr. 24, 1990

[54] ESOPHAGUS PROBE

[76] Inventors: Josef Reinhardt, Krozingerstrasse 10, D-7801 Ehrenkirchen; Martin Rössle, Hauptstrasse 71, D-7800 Freiburg, both of Fed. Rep. of Germany

[21] Appl. No.: 221,457

[22] PCT Filed: Oct. 27, 1987

[86] PCT No.: PCT/DE87/00486
 § 371 Date: Jun. 1, 1988
 § 102(e) Date: Jun. 1, 1988

[87] PCT Pub. No.: WO88/03034
 PCT Pub. Date: May 5, 1988

[30] Foreign Application Priority Data

Oct. 27, 1986 [DE] Fed. Rep. of Germany ....... 3636489

[51] Int. Cl.⁴ .............................................. A61N 1/05
[52] U.S. Cl. ..................... 128/785; 128/784
[58] Field of Search ............................... 128/784–787, 128/642, 303.17

[56] References Cited

U.S. PATENT DOCUMENTS 3,858,586 1/1975 Lessen ........................ 128/303.17 X
3,866,615 2/1975 Hewson ............................. 128/784
4,776,349 10/1988 Nashef et al. .................... 128/784 X

FOREIGN PATENT DOCUMENTS 0109935 5/1984 European Pat. Off. .
2140994 8/1971 Fed. Rep. of Germany .
2310775 11/1976 Fed. Rep. of Germany .
2822603 11/1979 Fed. Rep. of Germany .
3428644 8/1984 Fed. Rep. of Germany .
7537521 11/1975 France .
8200768 3/1982 PCT Int'l Appl. .
 602193 4/1978 U.S.S.R. .............................. 128/786

Primary Examiner—Lee S. Cohen
Attorney, Agent, or Firm—Jeffers, Hoffman & Niewyk

[57] ABSTRACT

An esophageal or gullet probe includes electrode points (13, 14) which can be stuck into the smooth muscles of the esophagus so that, by application of a stimulating current, contractions of the smooth muscles of the esophagus wall can be caused which in a hemorrhage of the esophageal veins enable a clamping of the veins extending through the wall of the esophagus.

14 Claims, 1 Drawing Sheet

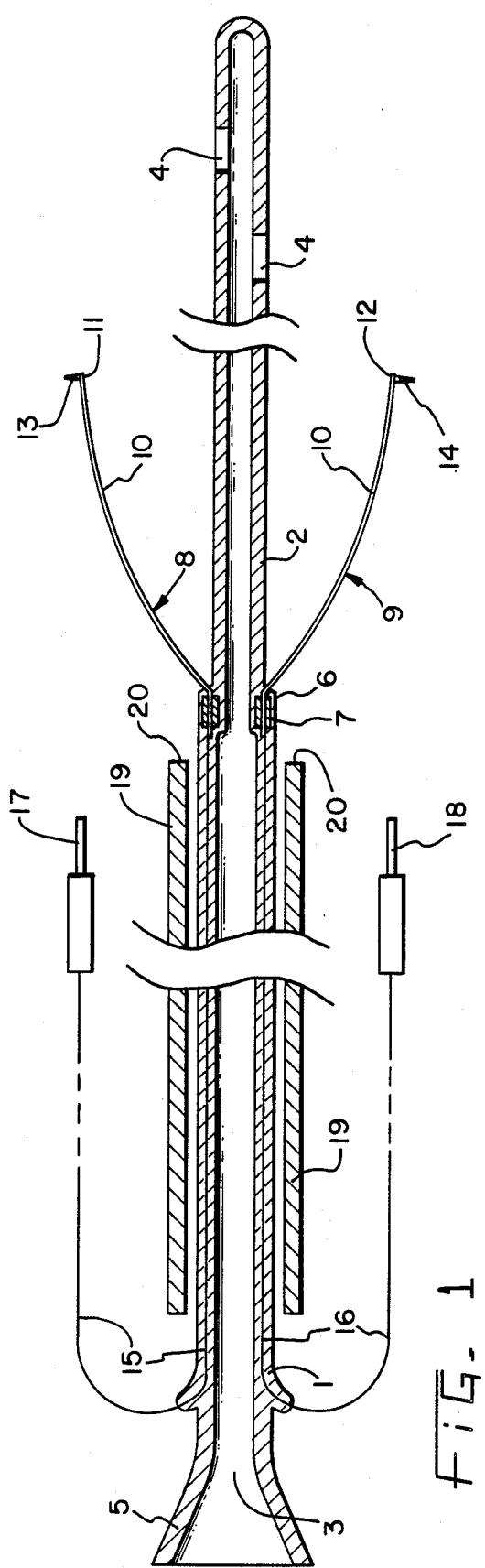
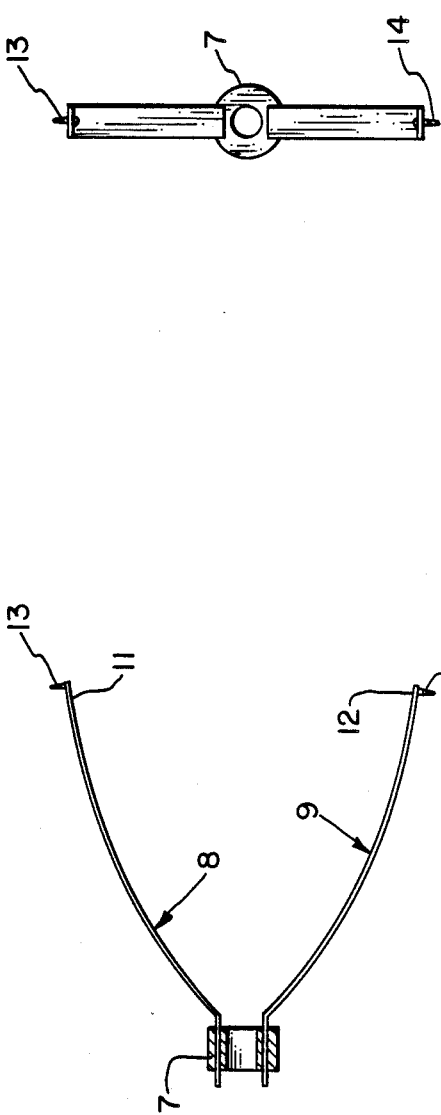

ESOPHAGUS PROBE

The invention concerns an esophagus probe with a tubus that can be advanced in the esophagus of a patient and which is provided with a device for stopping an esophageal hemorrhage.

An esophagus probe of that type where the device for stopping the bleeding consists of an inflatable espohagus balloon is the so-called Sengstaken-Blakmore probe. In addition to the inflatable esophagus balloon, this probe comprises an inflatable gastric balloon by which the distal end of the probe is secured inside the stomach. To the proximal end of the probe, which protrudes out of the patient's nose, a weight is attached so as to insure a constant position of the probe.

By inflating the esophagus balloon in the gullet, the bleeding veins of the esophagus wall are compressed, thereby achieving a stoppage of the bleeding.

But the prior probe is associated with a number of risks and inconveniences to the patient. Above the esophagus balloon, secretion and blood may accumulate. Severe aspiration pneumonia may occur due to drainage into the lung. Another source of danger is constituted by the fact that in the event of a bursting of the gastric balloon, which serves as an abutment for the weight forces, the probe may be pulled out of the esophagus by the weight arranged on the proximal end. The result may be a blockage of the entrance to the windpipe by the esophagus balloon which is still inflated.

Another disadvantage of the prior probe is that the constant pressure of the two balloons on the mucous membranes of the stomach and the windpipe may cause damage to the mucous membrane and ulceration. The ulcers may again be a source of bleeding.

When the bleeding of the dilated veins in the esophagus, which for instance may have occurred due to a cirrhosis of the liver, has been stopped, the probe needs to be removed. This involves often considerable difficulties because the probe sticks to the esophagus wall due to coagulated blood and often must be mobilized by heavy pull. Renewed varices bleeding occurs in more than 60% of all cases immediately after removal of the probe.

Basing on this prior art, the invention seeks to provide an esophagus probe where the risks and inconveniences to the patient are avoided.

This problem is inventionally solved in that the device is an electrode pair which is arranged on the tubes and can be forced on the mucous membrane of the esophagus while connected with an apparatus which delivers an electrical stimulating current.

The invention bases on the insight that the esophagus wall consists in its bottom third of smooth muscles. Such muscles are capable of performing contractions, that is, contractions of long duration. These are generated in the case of the inventional probe by application of an electrical stimulus. The voltage required for that purpose depends on the type of electrodes and on the local resistance. The optimal shape and size of the electrodes and the optimum frequency of the alternating or rectangular pulse current with alternating polarity pulses to be applied can be determined easily by experiments.

The contraction of the muscles or an increased muscle tonus of the esophagus of long duration causes a clamping of the veins extending through the esophagus wall. The hydrostatic pressure of this vein ranges in cirrhosis patients between 20 and 40 mmHg. The esophagus wall can through electrical stimulation easily produce a pressure of 100 to 200 mmHg.

In the presence of an esophageal varices bleeding, the probe—consisting of elastic material—is inserted through the nose into the esophagus while the patient is in a lying or standing position. The correct localization of the probe part that is provided with the electrode pair can either be estimated through a centimeter scale which is provided on the probe or can be determined accurately by x-ray. In acute emergencies it is sufficient to advance the probe by a specific measure, for instance by 45 cm. Once the probe has reached the intended position in the esophagus, the electrodes of the electrode pair are pierced into the mucous membrane of the esophagus and a stimulating current is applied.

In a preferred embodiment of the invention, the electrodes are arranged on electrode carriers which can be spread radially outward. The electrode carriers consisting of spring steel and are covered by a tubus as the probe is inserted, which releases the electrode carriers as it is retracted, thereby enabling a contacting for a stimulating current treatment. Preferably designed as electrode points, the electrodes penetrate the esophageal mucous membrane in the process and lie with their ends in the esophageal muscle. The stimulating current on the electrodes causes a contraction of the esophagus, thereby clamping the bleeding veins in the esophagus wall. Upon completion of the therapy, the probe is removed in a simple manner by slipping the tubus over the electrode carriers, thereby disengaging the electrodes from the esophagus wall. The probe can then be removed under light traction.

Favorable embodiments and developments of the invention are characterized in the subclaims.

An embodiment of the invention will be more fully explained hereafter with the aid of the drawing.

FIG. 1 shows an esophagus probe according to the invention in longitudinal section;

FIG. 2, the electrode carriers of the probe according to FIG. 1 with a stiffening ring supporting them, in longitudinal section and as a side elevation; and FIG. 3, the stiffening ring illustrated in FIG. 2 with the electrode carriers in a view in axial direction.

An esophagus probe or gullet probe illustrated in longitudinal section in FIG. 1 features a tubus 1 made from a plastic material and having a length of at least one-half meter while on the distal end extending into an extension tubus 2. A channel 3 with which there are coordinated in the extension tubus 2 several radial openings 4 and on the proximal end of the tubus 1 a fitting 5, extends through the tubus 1 and the extension tubus 2. When using the esophagus probe in a patient with esophageal varices bleeding it is possible to suck blood out of the stomach, through the extension tubus 2 and the openings 4, with the air of a pump connected to the fitting 5. This makes it possible to check whether the hemorrhage of the esophageal veins has come to a stand-still.

Embedded in the transitional range 6 between the tubus 1 and the extension tubus 2 is a stiffening ring 7 which serves the mounting of a first electrode carrier 8 and a second electrode carrier 9. The electrode carriers consist of spring steel and are radially opposed with regard to the stiffening ring 7 and the tubus 1. In the stiffening ring 7, the electrodes 8, 9 extend parallel with each other and angle radially outward after issuing out of the stiffening ring 7. This is illustrated separately in FIG. 2.

The electrode carriers 8, 9 are covered with an insulation 10 extending up into the vicinity of the free ends 11, 12 of the electrode carriers 8, 9. Provided on the free ends 11, 12 of the electrode carriers 8, 9 are electrode points 13, 14 which protrude radially outward and can be stuck into the mucous membrane of the esophagus under the spring effect of the spring steel of the electrode carriers 8, 9.

The electrode carrier 8, 9 ends embedded in the stiffening ring 7 connect through lines 15, 16 with plug type contacts 17, 18 which can be inserted in the output jacks of a stimulating current apparatus which is not illustrated in the drawing. The stimulating current apparatus is a rectangular pulse signal generator that delivers rectangular pulses with an adjustable frequency and an adjustable voltage. The frequency is adjustable between approximately 5 Hz and 50 Hz. The output voltage has an adjustable level between 0.5 and 8 volts.

As can be seen from FIG. 1, a tubus 19 of approximately the same length is mounted axially movable on the tubus 1. Basing on the position illustrated in FIG. 1, the tubus 19 can be advanced to the right, by retaining the tubus 1 in the area of the fitting 5 and exerting an axial pressure on its proximal end, until the end face 20 of the tubus 19 makes contact with the bowed electrode carriers 8, 9. As it is advanced further, the tubus 19 envelopes the electrode carriers 9, compressing them against the spring effect of the spring steel radially inward toward the extension tubus 2. The limit position is reached when the electrode carriers 8, 9 and the electrode points 13, 14 are completely surrounded by the tubus 19.

When the tubus 19 covers the electrode points 13, 14 in its completely advanced position, the esophagus probe can in the presence of an esophageal varices hemorrhage be inserted in the esophagus through the nose of a sitting or prone patient.

The proper localization of the transitional area 6 where the electrode carriers 8,9 for the electrode points 13, 14 are mounted can either be estimated by a centimeter scale provided on the probe or can be determined exactly by x-ray examination. In acute emergencies it will mostly be sufficient to advance the esophagus probe by approximately 45 cm.

Upon insertion of the esophagus probe in the gullet, the tubus 19 is retracted relative to the tubus 1, thereby causing the electrode characters 8, 9 to spread out radially under their spring force. In the process, the electrode points 13, 14 penetrate the mucous membrane of the esophagus and extend up into the smooth esophageal muscles.

As soon as contact has been made with the smooth muscles of the esophagus, the stimulating current apparatus is activated, impressing an alternating current with rectangular pulses into the electrode points 13, 14 and thus into the smooth muscles. The necessary voltage depends on the type and dimension of the electrode points as well as the local resistance of the muscles. The optimal shape and size of the electrodes as well as the optimal frequency of the alternating or rectangular current to be applied can be determined easily by experiments. It has been demonstrated that voltages in the order of several volts and frequencies of about 20 Hz are suited to trigger in the smooth muscles of the esophagus, through electrical stimulation, contractions of long duration. Generated by dispensation of an electrical stimulus, these contractions or an electrically triggered muscle tonus increase of long duration cause a clamping of the veins extending through the esophagus wall. The latter can easily produce a pressure of 100 to 200 mmHg, which exceeds the pressure in the veins of about 20 to 40 mmHg. Whether a final stoppage of the bleeding has been achieved can specifically be checked when blood is no longer being sucked through the channel 3.

After the completion of the therapy, the esophagus probe can be removed easily by sliding the tubus 19 forward and, as its end face 20 makes contact with the electrode carriers 8, 9, retracting the electrode points 13 from the muscles after the stimulating apparatus has been disconnected. Once the tubus 19 covers the sharp electrode points 13, 14, the esophageal tubus can be removed from the esophagus without resistance.

Illustrated in FIG. 3 is a plan view of the stiffening ring 7 and the electrode carriers 8, 9 viewed from the proximal end of the esophagus probe. As can be seen from FIG. 3, the electrode carriers are of a strip type design, the width of the strips ranging about in the order of the radius of the stiffening ring 7. Also recognizable in FIG. 3, protruding from the electrode carriers 8, 9, are the electrode points 13, 14, which preferably are made from precious metal which is compatible with the body.

We claim:

1. An apparatus for stopping esophageal bleeding, comprising:
    an esophageal probe with a first tubus adapted for advancing into the esophagus of a patient;
    an electrode pair arranged on said first tubus, said electrode pair including at least one sharp point projecting outwardly of said first tubus;
    a means for penetrating a mucous membrane of the esophagus by urging said at least one point into the membrane; and
    a stimulating current means for delivering an electrical stimulating current to said at least one point.

2. The apparatus according to claim 1, wherein said electrode pair includes a pair of electrode carriers, first ends of each of said electrode carriers including a sharp point, said electrode carriers mounted on said first tubus and being radially opposed.

3. The apparatus according to claim 2, wherein said electrode carriers are made from a material which springs radially outward.

4. The apparatus according to claim 3, wherein said electrode carriers consist of spring steel.

5. The apparatus according to claim 2, wherein second ends of said electrode carriers located away from said points are attached to a stiffening ring that is embedded in said first tubus.

6. The apparatus according to claim 1, further comprising a second tubus which is flexible and stressible in longitudinal direction, said second tubus being movably mounted on said first tubus, a distal end of said second tubus covering said at least one point while said tubus is in an advanced position, and, while in a retracted position, exposing said at least one point.

7. The apparatus according to claim 1, wherein said first tubus includes a fitting located on a proximal end of said first tubus, and an extension tubus located on a distal end of said first tubus, said extension tubus provided with a plurality of radial openings.

8. The apparatus according to claim 1, wherein said stimulating current means comprises electrical contacts adapted to be connected to a rectangular pulse generator which delivers rectangular pulses which alternate in polarity and have an adjustable frequency and adjustable voltage.

9. An esophageal probe including a first tubus adapted for advancement into the esophagus of a patient for stopping an esophageal varices bleeding, said first tubus having an electrode pair mounted thereon which can be forced against a mucous membrane of the esophagus and is adapted to be connected to a stimulating current apparatus which delivers an electrical stimulating current, said electrode pair including electrode points projecting outwardly of said first tubus, said electrode points having means for penetrating the mucous membrane of the esophagus, a second tubus movably mounted on said first tubus, said second tubus being flexible, a distal end of said second tubus adapted to cover said electrode points in a first position of said second tubus and exposing said electrode points in a second position of said second tubus.

10. The esophageal probe according to claim 9 wherein said electrode pair includes a pair of electrode carriers, said electrode points are arranged on first ends of said electrode carriers which are mounted in radially opposed positions on said first tubus.

11. The esophageal probe according to claim 10 wherein said electrode carriers are made from a resilient material.

12. An esophageal probe having a first tubus adapted for advancement into the esophagus of a patient and which includes a device for stopping an esophageal varices bleeding, said device being mounted on said first tubus and including an electrode pair which can be forced against a mucous membrane of the esophagus and is adapted to be connected to a stimulating current apparatus which delivers an electrical stimulating current, each electrode of said electrode pair including an electrode point projecting outwardly of said first tubus, said electrode points having means for penetrating the mucous membrane of the esophagus, said first tubus including a fitting on a proximal end of said first tubus, and an extension tubus on a distal end of said first tubus, said extension tubus provided with a plurality of radial openings.

13. The esophageal probe according to claim 12 wherein said electrode pair includes a pair of electrode carriers, said electrode points are arranged on first ends of said electrode carriers which are mounted in radially opposed positions on said first tubus.

14. The esophageal probe according to claim 13 wherein said electrode carriers are made from a spring steel material.

* * * * *